(12) United States Patent
Shinohara et al.

(10) Patent No.: US 7,272,969 B2
(45) Date of Patent: Sep. 25, 2007

(54) ABRASION TESTER AND TEST METHOD

(75) Inventors: Kenichi Shinohara, Tochigi (JP);
Teisuke Bushimata, Tokyo (JP)

(73) Assignee: E. I. du Pont de Nemours and Company, Wilmington, DE (US)

( * ) Notice: Subject to any disclaimer, the term of this patent is extended or adjusted under 35 U.S.C. 154(b) by 169 days.

(21) Appl. No.: 10/992,017

(22) Filed: Nov. 18, 2004

(65) Prior Publication Data
US 2005/0120774 A1 Jun. 9, 2005

Related U.S. Application Data

(60) Provisional application No. 60/527,573, filed on Dec. 5, 2003.

(51) Int. Cl.
*G01N 3/56* (2006.01)
(52) U.S. Cl. .......................................................... 73/7
(58) Field of Classification Search ........................ 73/7
See application file for complete search history.

(56) References Cited

U.S. PATENT DOCUMENTS 4,722,218 A 2/1988 Strader et al.

4,939,922 A 7/1990 Smalley et al.

FOREIGN PATENT DOCUMENTS

| JP | 54-145584 | 11/1979 |
| SU | 560166(A1) | 5/1977 |
| SU | 1516882(A1) | 10/1989 |

OTHER PUBLICATIONS

"Polymers, An Encyclopedic Sourcebook of Engineering Properties", Encyclopedia Reprint Series, John C. Wiley & Sons, Inc., 1987, pp. 8-11.
Tribology Data Book (Techno System Shuppan, 1991), pp. 195-205 (translation).
International Search Report for PCT/US2004/040633 dated Apr. 25, 2005.

*Primary Examiner*—Robert Raevis

(57) ABSTRACT

An apparatus for testing abrasion and a test method for testing the frictional wear characteristics of materials and parts even when a lubricant is used. The abrasion and test method enables reliable abrasion tests to be carried out in which good conformity with the sliding characteristics in actual pieces of equipment can be achieved.

2 Claims, 3 Drawing Sheets

ABRASION TESTER AND TEST METHOD

CROSS REFERENCE TO RELATED APPLICATION

This application claims the benefit of U.S. Provisional Application No. 60/527,573, filed Dec. 5, 2003.

FIELD OF THE INVENTION

The present invention relates to an abrasion tester and a test method for measuring the frictional wear characteristics of various types of materials, including metals, plastics, ceramics and rubbers. More particularly, the present invention relates to a sliding abrasion tester and test method that can perform highly reliable abrasion tests that conform well to the sliding characteristics in an actual piece of equipment.

BACKGROUND OF THE INVENTION

The following disclosures may be relevant to various aspects of the present invention and may be briefly summarized as follows:

Many testers and test methods for evaluating the frictional wear characteristics of materials and lubricants are known in the art. The prior art reference entitled "Polymers, An Encyclopedic Sourcebook of Engineering Properties", Encyclopedia Reprint Series, John Wiley & Sons Inc., copyright 1987 pgs. 8-11, discloses a variety of devices and ASTM standards for test procedures for frictional wear.

Tribology Data Book (Techno System Shuppan, 1991). pgs. 195-205 describes various types of abrasion tests and their features, including pin-on-disk type, thrust cylinder type and block-on-ring type testers. The reference also mentions that it is common for measurement to be carried out under a fixed contacting load and a fixed friction speed.

JP-A 54-145584 is aimed at the measurement and evaluation of frictional resistance in a test specimen subjected to a fluctuating load under the same conditions as an actual piece of equipment that employs a reciprocating sliding mechanism. This reference discloses a tester, which uses an eccentric cam in order to vary as desired the sliding velocity, the contacting load, and the fluctuating load and period.

U.S. Pat. No. 4,939,922 to Smalley et al. discloses a technique for measuring the sliding characteristics between two test specimens that slide relative to each other while remaining in mutual contact. One of the test specimens being rotated by means of a rotary drive unit via an eccentric cam and the other test specimen being pressed against the first test specimen by an elastic body.

The testers and test methods disclosed in the prior art have the drawback that the sliding results obtained from the tests do not always conform well with the sliding characteristics of components in actual pieces of (e.g. commercial) equipment. This is believed to be attributable to the following reasons. In commercial or actual pieces of equipment: (1) the load and the sliding velocity are often not uniform, but instead vary periodically within a range; (2) because the test is carried out with the test specimens constantly in a state of mutual contact, the frictional heat generated builds up in the area of contact and the frictional wear behavior is strongly affected by the ensuing rise in temperature; and (3) because powder generated by abrasion builds up on the contact surfaces, the measured amount of wear does not directly represent the wear properties of the material.

Furthermore, in sliding-type abrasion tests in which a lubricating oil or grease is applied to the contact surface of the test specimen, the coefficient of friction is quite low, very little wear occurs, hence clear differences are often not obtained in measurement making it difficult to achieve worthwhile test results. In various electrical products for industrial or consumer applications, including drive system motors employed in automotive electrical components, sliding mechanism components are generally used with a lubricating oil or grease on the contact surfaces. Accordingly, there is a desire for an abrasion tester which can measure and evaluate the frictional wear characteristics of such components in a state that is the same as or similar to the conditions of actual use and which provides a higher reliability that makes it possible to predict the life of a product, thus enabling suitable material selection or design to be carried out.

SUMMARY OF THE INVENTION

Briefly stated, and in accordance with one aspect of the present invention, there is provided an apparatus for testing abrasion comprising:
  a sample holder for holding a test specimen;
  a pressing means to generate frictional wear between a surface of the pressing means and a surface of the test specimen; and
  a drive unit coupled to the pressing means, where the drive unit effects movement of the pressing means along a plane on the surface of the test specimen while the pressing means applies a given pressing force to the test specimen, wherein the pressing means is a cam having an axis of rotation at its center and a surface located a distance (d) from the axis of rotation, the cam characterized by having: a minimum distance (d1) from the axis of rotation to a point on the surface of the cam and a maximum distance (d2) from the axis of rotation to a point on the surface of the cam, the axis of rotation positioned a given distance (L) from the surface of the test specimen, wherein d1<L<d2, the cam being rotated by the drive unit about the axis of rotation and intermittently coming into direct contact with the test specimen when L is less than or equal to (d), and controlled to press against the test specimen in such a way that a maximum pressing force is fixed; and wherein the sample holder, by means of an elastic member coupled thereto, allows the test specimen to be displaced with respect to the pressing means in response to the pressing force applied to the test specimen.

Pursuant to another aspect of the present invention, there is provided an abrasion test method comprising the steps:
  (a) using an apparatus for testing abrasion to hold a test specimen with the apparatus sample holder, wherein the apparatus comprises (i) a sample holder for holding a test specimen: (ii) a pressing means to generate frictional wear between a surface of the pressing means and a surface of the test specimen; and (iii) a drive unit coupled to the pressing means, where the drive unit effects movement of the pressing means along a plane on the surface of the test specimen while the pressing means applies a given pressing force to the test specimen, wherein the pressing means is a cam having an axis of rotation at its center and a surface located a distance (d) from the axis of rotation, the cam characterized by having: a minimum distance (d1) from the axis of rotation to a point on the surface of the cam and a maximum distance (d2) from the axis of rotation to a point on the surface of the cam, the axis of rotation positioned a given distance (L) from the surface of the test specimen, wherein d1<L<d2, the cam being rotated by the drive unit about the axis of rotation and intermittently coming into direct contact with the test specimen when L is less than or equal to (d), and controlled to press against the test specimen in such a way that a maximum pressing force is fixed; and wherein the sample holder, by means of an elastic member coupled thereto, allows the test specimen to be displaced with respect to the pressing means in response to the pressing force applied to the test specimen;

and (b) using the drive unit and pressing means of the apparatus to effect movement of the pressing means on a surface of the test specimen while the pressing means applies a given pressing force to the test specimen to generate frictional wear between the pressing means and the test specimen.

BRIEF DESCRIPTION OF THE DRAWINGS

The invention will be more fully understood from the following detailed description, taken in connection with the accompanying drawings, in which.

Figure 1:
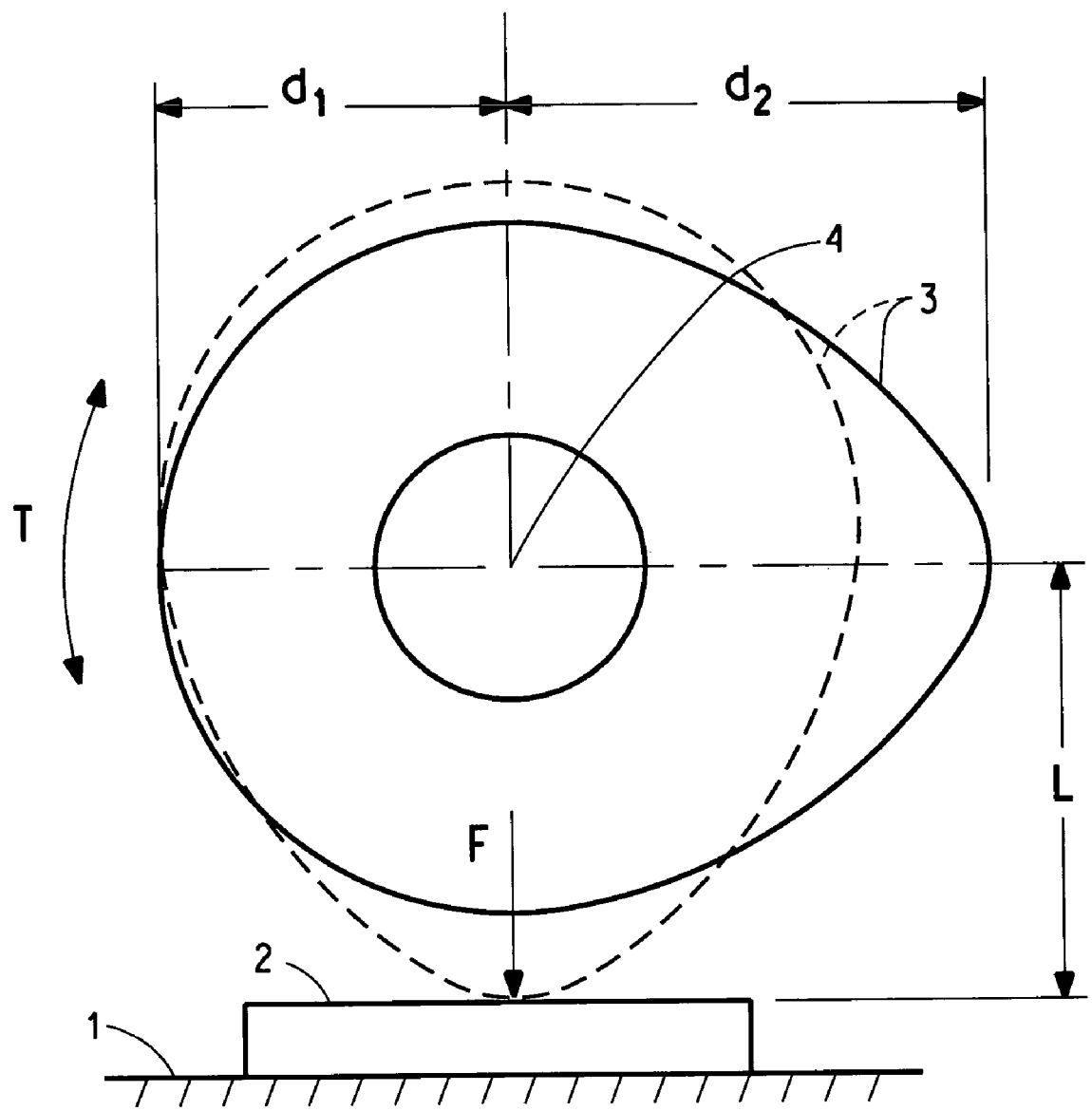
FIG. 1 is a schematic illustrating the relationship between the cam of the abrasion tester of the present invention and a test specimen.

While the present invention will be described in connection with a preferred embodiment thereof, it will be understood that it is not intended to limit the invention to that embodiment. On the contrary, it is intended to cover all alternatives, modifications, and equivalents as may be included within the spirit and scope of the invention as defined by the appended claims.

DETAILED DESCRIPTION OF THE INVENTION

As mentioned above, the prior-art sliding-type abrasion testers and test methods do not conform well to the sliding characteristics in actual pieces of equipment. Consequently, agreement between frictional wear experienced in actual equipment (i.e. various automotive and electrical applications including drive system motors employed in automotive electrical components) and the results obtained using such abrasion testers is poor. Moreover, such test results vary widely depending on the tester and the conditions of use, thus compromising reproducibility. It has thus previously been extremely difficult if not impossible to reliably measure the frictional wear characteristics until the present invention.

The present invention encompasses two elements: an abrasion tester and a method of testing abrasion. One element of the present invention provides an abrasion tester having a sample holder for holding a test specimen, a pressing device which is pressed against the test specimen to generate frictional wear between itself and the test specimen, and a drive unit which is coupled to the pressing device. The drive unit effects given movement (i.e. pressing movement) of the pressing device within the plane of the test specimen while the pressing device applies a pressing force to the test specimen generated by drive unit movement); wherein the pressing device is a cam which has a minimum distance to the cam central axis of rotation (d1) and a maximum distance to the cam central axis of rotation (d2), which has a central axis of rotation positioned a given distance (L) from the surface of the test specimen, which is rotated by the drive unit about the central axis of rotation and intermittently comes into direct contact with the test specimen when d1<L<d2, and which is controlled to press against the test specimen in such a way that the maximum stress at the time of contact is fixed; and wherein the sample holder, by means of an elastic member coupled thereto, allows the test specimen to be displaced with respect to the pressing device in response to the pressing force that is applied to the test specimen.

A second element of the present invention provides an abrasion test method which includes holding a test specimen with a sample holder, pressing a pressing device against the test specimen to generate frictional wear between itself and the test specimen, and using a drive unit coupled to the pressing device to effect given movement of the pressing device within the plane of the test specimen while the pressing device applies a given pressing force to the test specimen; the method being characterized in that the pressing device is a cam which has a minimum distance to the cam central axis of rotation (d1) and a maximum distance to the cam central axis of rotation (d2), which has a central axis of rotation positioned a given distance (L) from the surface of the test specimen, which is rotated by the drive unit about the central axis of rotation and intermittently comes into direct contact with the test specimen when d1<L<d2, and which is controlled to press against the test specimen in such a way that the maximum stress at the time of contact is fixed; and also being characterized in that the sample holder, by means of an elastic member coupled thereto, allows the test specimen to be displaced with respect to the pressing device in response to the pressing force applied to the test specimen.

Reference is now made to the drawings for a detailed description of the present invention. FIG. 1, shows a schematic illustrating the relationship between the cam 3 on the abrasion tester of the present invention and a test specimen 2. In the abrasion tester and test method of the present invention, the pressing device is a cam 3 having at least one lobe of maximum, distance to the cam central axis of rotation d2, which contacts the test specimen 2 that has been placed on a sample holder 1. When the relationship d2>L>d1 between the minimum distance (d1) and the maximum distance (d2) of the cam 3 with respect to the distance (L) from the center axis to the surface of contact with the opposing material of the test specimen 2 is satisfied, rotation of the cam 3 generates a stress that fluctuates intermittently or periodically on the surface of contact, thus enabling the reproduction of wear behavior which more closely approximates the conditions encountered in an actual piece of equipment.

Because the shape of the non-circular cam 3 satisfies the condition that the maximum distance (d2) exceeds the distance (L) from the axis of rotation to the surface of the opposing material of the test specimen 2, the portion of the cam 3 near the end of maximum length (d2) comes into contact with the surface of the opposing material of the test specimen 2 and presses against it. In response to the pressing force applied to the test specimen 2 on the sample holder 1, there is generated an elastic force of repulsion by an elastic member (not shown in FIG. 1) coupled to the sample holder 1. Because (d1) is shorter than the distance (L) from the axis of rotation 4 to the surface of the opposing material of the test specimen 2, the cam 3 is at times not in contact with the opposing material surface of the test specimen. This is shown by the solid line illustration of cam 3 in FIG. 1. When the cam 3 is rotated about its center axis 4, contact begins near a point where the distance (d) from the cam surface to the center is equal to the distance (L) from the center to the opposing material surface of the test specimen. This rotated cam in contact with the test specimen surface is shown by the dotted line illustration of the cam in FIG. 1. At the point where the cam center is at a maximum distance (d2) from the specimen surface, the cam presses the opposing material on the surface of the test specimen downward a distance of exactly (d2−L), generating a maximum stress which corresponds to the pressing amount. Contact between the cam and the specimen begins and continues under the condition that the distance (L) is less than or equal to the distance (d). When the cam 3 is continuously rotated, from the time at which contact between the test specimen 2 surface and the cam 3 begins to the time at which this contact again ends, the stress at the point of contact changes from zero to a maximum stress value and back to zero. The maximum stress can be adjusted according to sample thickness and initial load of the elastic body spring under the test specimen. This cycle is repeated intermittently. The pressing force (F, shown in FIG. 1), generated against the surface of the test specimen 2 by the cam 3 due to elastic deformation corresponding to the change in the distance of the specimen surface to the axis of rotation of the cam, is accompanied by frictional forces generated by sliding motion on the surface of contact.

In the present invention, the maximum stress can be tested over a wide range. The range can be from 0 to 500 N and above, depending upon the sample thickness and the spring load. For example in an application such as a power steering gear, the surface contact force by gear engage is 200-400 N in pushing force. Reference is made to FIG. 3, which provides a practical example of about 300 N pushing force. The wear tester of the present invention can also generate higher pushing force up to 500 N or above, by increasing the test specimen (e.g. when the sample thickness is about 6 mm, the maximum pushing force should be 535 N), and changing the spring to a higher spring constant (The spring constant can be modified by the following spring equation: $K=G \times d^4/8 \times n \times D^3$ where G: elastic modulus of metal spring, d: diameter of spring coil, D: average coil diameter, n: number of winds) or by giving an initial tension at the spring by pushing up the supporting base (20 in FIG. 2) upward. Preferably the higher pushing force generated by the wear tester of the present invention is 500 N and above.

With continued reference to FIG. 1, in the practice of the present invention, when the relationship d2>L>d1 of the minimum distance (d1) and the maximum distance (d2) with respect to the distance (L) from the center axis 4 of the cam 3 to the surface of contact on the test specimen 2 is satisfied on the line that joins the shortest point from the cam axis of rotation 4 to the surface of the opposing test specimen 2, a force (F) is generated that presses down against the surface of the test specimen. The force generated on the opposing material of the test specimen surface is a surface stress force. Such generation of stress at the surface of the test specimen 2 may be achieved by, for example, 1) placing an elastic body such as a spring beneath the test specimen 2 on the opposing side of the sample holder or 2) having the test specimen cantilever out from one point of support or span two points of support. For example, the test specimen is similar to a bar, wherein a holder fixes one end of the bar and the bar moves up and down in response to the contact from the rotation of the cam. If the approach of example 1) is selected, a force can be generated which is a quantity obtained by multiplying the amount the test specimen 2 is pressed downward by a spring constant. In the practice of this embodiment of the present invention, a downward pushing force (F) is generated within a range of 0 to 500 N and above. If the approach of example 2) is selected, the test specimen can be fixed at one or both ends, and is set so that the other end or the center of the specimen is pressed downward by contact from the rotating cam, thereby generating a force which corresponds to the elastic constant of the test specimen 2.

If one wishes to directly measure the surface stress generated at the test specimen surface of contact in the test, one method is to embed a strain sensor on the inside of the contact area of the cam 3. Another method is to install a load cell at the bottom end of a supporting spring. These arrangements make it possible to monitor changes over time in the force applied to the test specimen surface of contact during the test.

In the invention, the cam has a curved surface. Theoretically, if this test specimen is a completely rigid body, the contact surface takes the form of point or line contact. The curved surface may be arched, elliptical or of some other shape. However, if the distance from the center of the axis of rotation 4 to the point of contact is known, the stress generated at each point of contact can easily be determined.

In the present invention, "intermittent" means that as the surfaces of the test specimen 2 and the cam 3 lobe are in frictional contact during rotation by the cam, there will be times in which the cam and the lobe are not in contact. Providing a time in which the test specimens 2 are in such a mutually separated state discourages a continuous rise in temperature due to frictional heat and also helps minimize secondary errors due to the constant buildup of powder generated by abrasion between the contact surfaces.

The cam shape in the present invention may have any number of lobes, insofar as the above-described relationship is satisfied. Even a simple eccentric cam is acceptable as long as it periodically generates a fixed stress at the surface of contact of the test specimen. Moreover, in the present invention, by changing the distance (L) between the axis of rotation and the contact surface of the test specimen 2, the frequency of contact and the contact stress can be easily adjusted. If the cam test specimen 2 in the present invention is made of metal or ceramic, it can be fabricated by an operation such as cutting, extrusion, casting or forging. If it is made of plastic or rubber, it can be fabricated by injection molding, extrusion or cutting (machining). Furthermore, in the abrasion test, because it is possible to measure the state of only the portion that comes into contact (e.g. the cam outer surface and the test specimen surface contact area), there is no need to make the entire cam out of the same material. The design may conceivably be one in which a curved surface made of the target material (i.e. the material desired to test friction and wear behaviors) is incorporated into a cam-shaped base material only at the area of contact with the test specimen surface. Examples of such methods that may be used include applying a thin film-like material onto the curved surface of the cam, or fitting a small component with a curved surface as an insert only at the area of contact with the surface of the test specimen material. These approaches are effective in, for example, cases where one wishes to comparatively examine various materials on the cam test specimen side because it eliminates the need to individually fabricate difficult-to-machine cams. Moreover, instead of furnishing standard test specimens for testing, sliding mechanism components are used directly on cams of the same types that are actually employed, thus enabling tests to be performed under the same conditions encountered in use on actual pieces of equipment.

Figure 2:
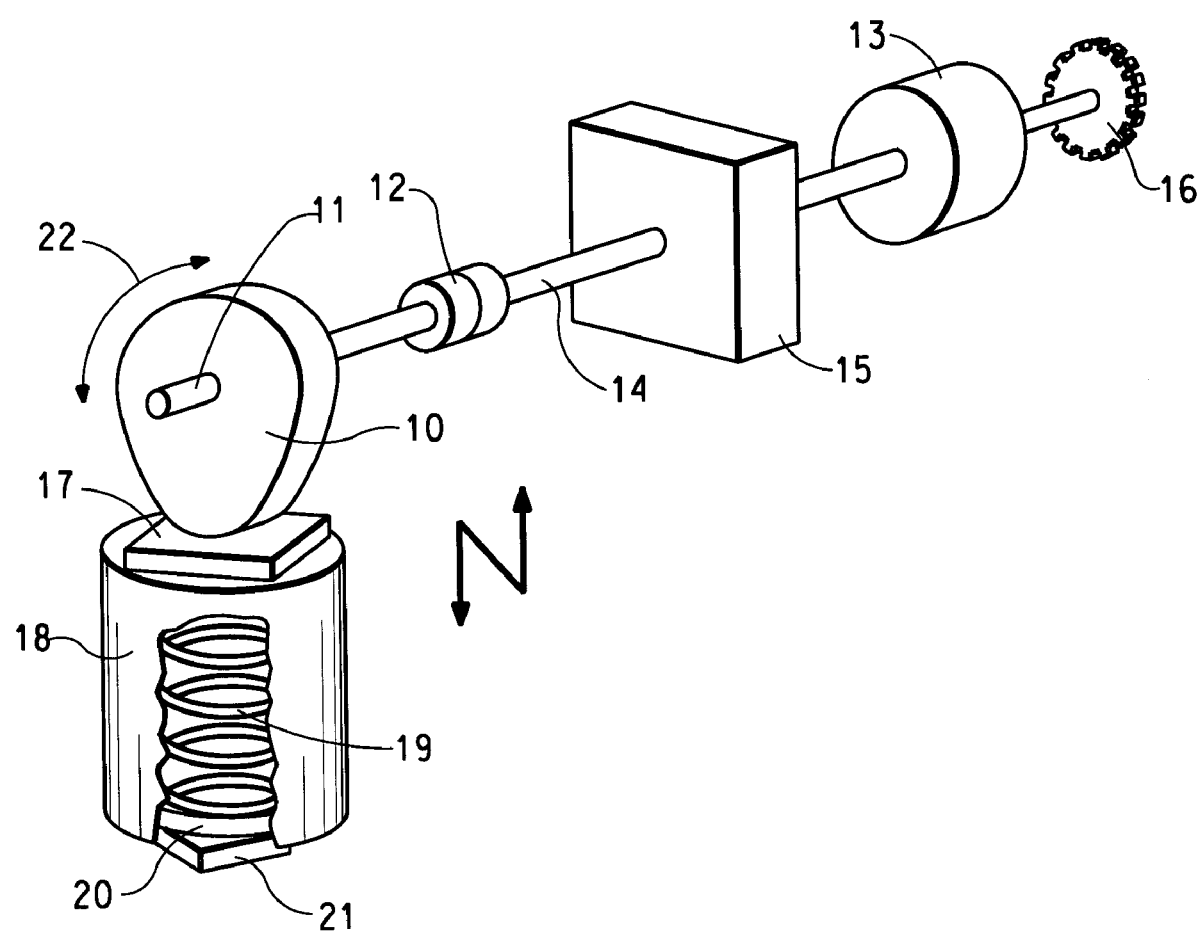
FIG. 2 is a schematic illustration of the present invention showing the main features of the abrasion tester of the present invention including a cutaway view of the coil spring contained in the cylindrical drum.

The measurement of frictional forces using the abrasion tester or test method of the present invention is briefly described. The frictional force generated when the cam slides over the surface of the opposing material can be determined by measuring the torque (T) (shown by the curved arrow 22 in FIG. 2) on the shaft that rotates the cam. (The rotation of the cam for the torque (T) can be either counterclockwise or clockwise in the present invention as shown in FIGS. 1 and 2.) The maximum dynamic coefficient of friction is calculated using the following equation:

$$\mu m = T \cdot (1/d2) \cdot (1/F)$$

where T is the measured rotational torque, d2 is the maximum distance from the axis of rotation (center) of the cam, and F is the perpendicular force applied to the contact surface. Changes in the frictional forces generated on the surface of contact can be tracked by monitoring the rotational torque over time using a torque sensor. Frictional forces that change when wear occurs, during a test or due to the depletion of lubricant, can be sensitively detected as changes in the rotational torque.

The rotational velocity of the cam can be monitored by installing a tachometer on the motor side. Even when the rotational speed is set to a fixed value initially, there will be times where the rotational speed changes as the coefficient of friction changes, thus monitoring the rotational speed is also necessary for reproducibility of the test results.

The present invention also enables tests for cases in which machine oil, grease, solid lubricant or the like is applied to the sliding area to be performed using a test method involving the application of lubricant to the test specimen. It is also possible to examine the process by which effects appear with increases in the generation of wear or the friction coefficient as the lubricant between the contact surfaces vanishes in the course of a test.

An embodiment of the abrasion tester and test method according to the invention is described in detail below in reference to FIG. 2, which is a schematic that shows the main features of the abrasion tester of the present invention and includes a cutaway view of part of the internal structure, and FIG. 3, which shows the results of frictional force measurements using the abrasion tester of the invention. FIG. 2 shows the main features of the abrasion tester of the invention, and includes also a cutaway view of part of the internal structure. Specifically, the diagram shows a cam 10, and a rotary shaft 11 that are linked to a motor 13 through a coupler 12. A motor shaft 14 on the motor 13 has a torque meter 15 and a digital tachometer 16 connected thereto, enabling constant measurement of the rotational speed and torque.

The cam 10 comes into contact with an opposing test specimen 17 that is fixed onto a cylindrical drum 18. The cylindrical drum 18 houses a coil spring 19 therein. Therefore, as the cam 10 moves the test specimen 17 vertically, a force of repulsion by the spring 19 arises at the surface of contact between the cam 10 and the test specimen 17. The force that occurs at the other end of the spring 19 is determined by a stress/strain gauge 21 that is attached therebelow to an intervening supporting base 20. Signals from the torque meter, tachometer and strain gauge are send to a computer and output with a recorder, making it possible to carry out a close analysis.

Figure 3A:
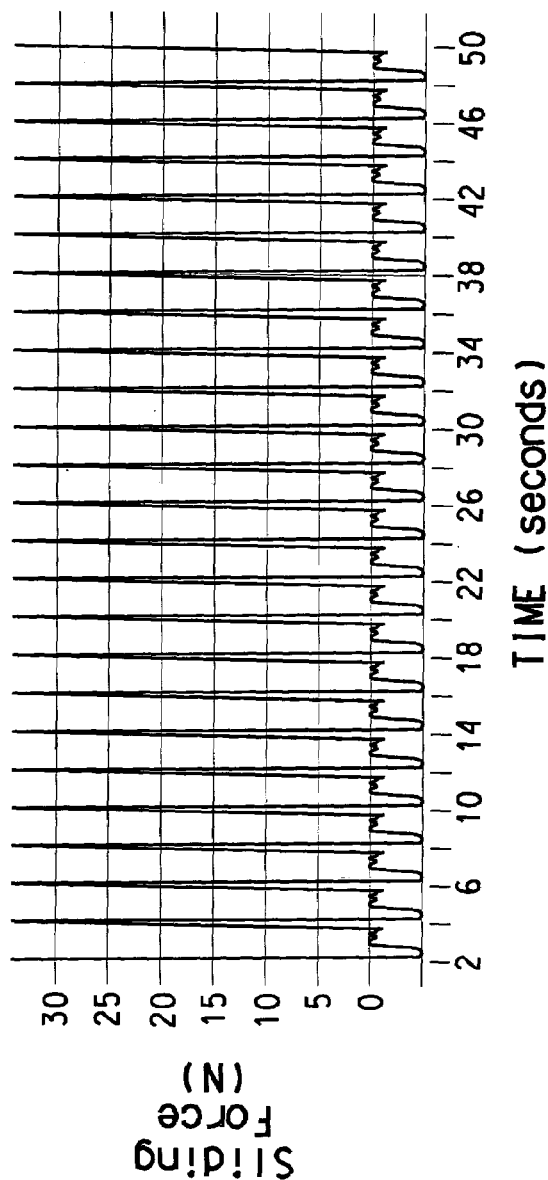
FIG. 3A and 3B show the graphical results of frictional force measurements using the present invention.
Figure 3B:
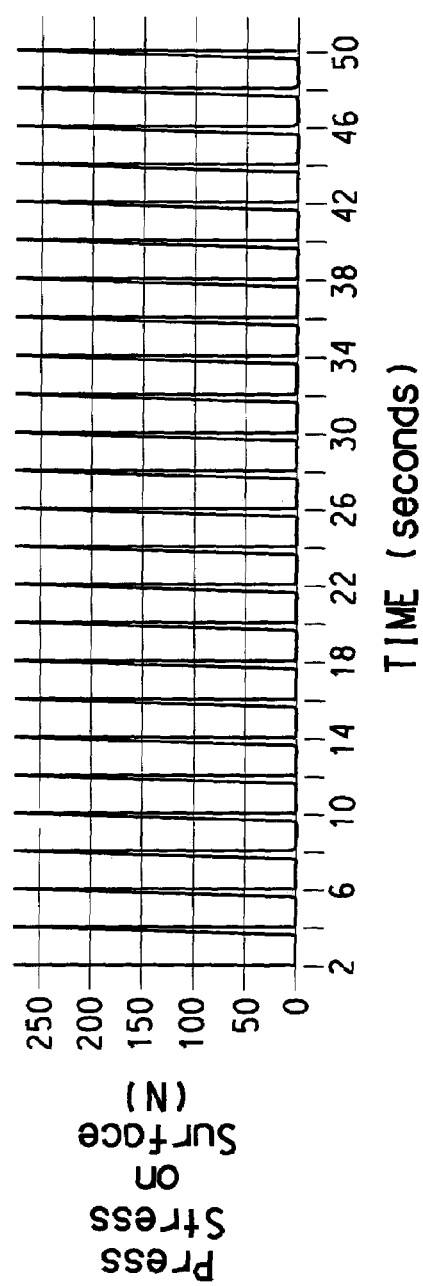

Reference is now made to FIGS. 3A and 3B which show the actual results obtained when the sliding characteristics for un-reinforced nylon, i.e. nylon 66 manufactured by E.I. duPont de Nemours & Co. of Wilmington, Del. in this example, was measured using the abrasion tester according to the invention. The graphical axis of FIG. 3A is the sliding force (newtons) by time (seconds). The sliding force below 0 in FIG. 3A results from the rebound effect of the elastic body movement (i.e. spring effect). The graphical axis of FIG. 3B is press stress on surface (N) versus time (seconds).

For the cam used in this case d1 was 12.5 mm and d2 was 16.5 mm. The cam was made of 5 mm thick S45C steel. The opposing material used was a test specimen 17 made of un-reinforced 6,6-nylon, applied by lithium-saponified grease on the contact surface. The distance from the camshaft to the test specimen 17 used as the opposing material was adjusted to 13.5 mm. The maximum planar stress applied perpendicular to the contact surface of the test specimen 17 was determined from the cam pressing amount (i.e. adjusted to about 3 mm) and the spring constant of the coil spring (i.e. 107 N/mm was used in this case) to be about 321 N. FIG. 3B shows the actual maximum load measurements (i.e. force peaks) are about 270 N, which is 51 N lower than 321 N due to the inertia effect of the elastic body (i.e. spring, see FIG. 2). In addition, the contact width over which the cam 10 contacted the opposing material surface of the test specimen 17 was calculated to be about 14.5 mm. The cam was set to a rotational speed of 30 rpm and the interval of stress peaks were two (2) seconds FIG. 3B shows the change in the pressure gauge at the bottom end of the coil spring. It is apparent from this that the maximum stress on the test specimen 17 when the cam 10 intermittently contacts the test specimen remains always fixed. FIG. 3A shows the sliding force induced from the rotational torque of the cam. It is apparent from this that the displacement of the pressure gauge 21 remains always constant during measurement, indicating that the stress applied to the contact surface remains fixed and unchanging.

As is also apparent from the measurement in this example, the use of the inventive abrasion tester enables subtle changes in the sliding mechanism to be tracked.

It is therefore, apparent that there has been provided in accordance with the present invention, an abrasion tester and test method that fully satisfies the aims and advantages hereinbefore set forth. While this invention has been described in conjunction with a specific embodiment thereof, it is evident that many alternatives, modifications, and variations will be apparent to those skilled in the art. Accordingly, it is intended to embrace all such alternatives, modifications and variations that fall within the spirit and broad scope of the appended claims.

The invention claimed is:

1. An apparatus for testing abrasion comprising:
   a sample holder for holding a test specimen;
   a pressing means to generate frictional wear between a surface of the pressing means and a surface of the test specimen; and
   a drive unit coupled to the pressing means, where the drive unit effects movement of the pressing means along a plane on the surface of the test specimen while the pressing means applies a given pressing force to the test specimen, wherein the pressing means is a cam having an axis of rotation and a surface located a distance (d) from the axis of rotation, the cam characterized by having: a minimum distance (d1) from the axis of rotation to a point on the surface of the cam and a maximum distance (d2) from the axis of rotation to a point on the surface of the cam, the axis of rotation positioned a given distance (L) from the surface of the test specimen, wherein d1<L<d2, the cam being rotated by the drive unit about the axis of rotation and intermittently coming into direct contact with the test specimen when L is less than or equal to (d), and controlled to press against the test specimen in such a way that a maximum pressing force is fixed; and wherein the sample holder, by means of an elastic member coupled thereto, allows the test specimen to be displaced with respect to the pressing means in response to the pressing force applied to the test specimen.

2. An abrasion test method comprising the steps:
(a) using the apparatus of claim 1 to hold a test specimen with the apparatus sample holder;
and (b) using the drive unit and pressing means of the apparatus to effect movement of the pressing means on a surface of the test specimen while the pressing means applies a given pressing force to the test specimen to generate frictional wear between the pressing means and the test specimen.

* * * * *